US009955682B2

(12) United States Patent
Kravitz et al.

(10) Patent No.: US 9,955,682 B2
(45) Date of Patent: May 1, 2018

(54) PORTABLE ORGAN TRANSPORTATION SYSTEM

(75) Inventors: David Kravitz, Barrington Hills, IL (US); Aaron Randall Ferber, Chicago, IL (US); Ross Lockwood, Chicago, IL (US); Rodney Hal Monson, Waukegan, IL (US); Evan David Shapiro, Chicago, IL (US)

(73) Assignee: LIFELINE SCIENTIFIC, INC., Itasca, IL (US)

( * ) Notice: Subject to any disclaimer, the term of this patent is extended or adjusted under 35 U.S.C. 154(b) by 271 days.

(21) Appl. No.: 13/097,809

(22) Filed: Apr. 29, 2011

(65) Prior Publication Data
US 2012/0276620 A1 Nov. 1, 2012

(51) Int. Cl.
*A01N 1/02* (2006.01)
*B62B 3/10* (2006.01)
*B62B 3/02* (2006.01)

(52) U.S. Cl.
CPC ......... *A01N 1/0236* (2013.01); *A01N 1/0247* (2013.01); *B62B 3/02* (2013.01); *B62B 3/10* (2013.01); *B62B 2202/42* (2013.01); *B62B 2206/06* (2013.01); *Y10T 29/49815* (2015.01)

(58) Field of Classification Search
CPC ....... B62B 5/0016; B62B 5/00; B62B 3/1472; B62B 3/04; A01N 1/0273
See application file for complete search history.

(56) References Cited

U.S. PATENT DOCUMENTS

| 4,186,565 | A | * | 2/1980 | Toledo-Pereyra | ....... A01N 1/02 435/284.1 |
|---|---|---|---|---|---|
| 5,215,210 | A | * | 6/1993 | Ostrum | ................ B65D 25/325 220/754 |
| 5,586,438 | A | * | 12/1996 | Fahy | ........................ A01N 1/02 435/284.1 |
| 5,967,362 | A | * | 10/1999 | Corbin | .................. B65F 1/1468 220/648 |
| 6,012,729 | A | * | 1/2000 | Lin | ........................ B62B 1/125 280/37 |
| 6,046,046 | A | | 4/2000 | Hassanein | |
| 6,116,461 | A | * | 9/2000 | Broadfield et al. | ............. 221/98 |
| 6,431,319 | B1 | | 8/2002 | Myers et al. | |
| 6,673,594 | B1 | | 1/2004 | Owen et al. | |
| 8,079,559 | B1 | * | 12/2011 | Say | ........................... A47L 5/24 248/221.11 |
| 2004/0224299 | A1 | * | 11/2004 | Garland | .................. A01N 1/02 435/1.2 |

(Continued)

FOREIGN PATENT DOCUMENTS

CN 101072500 A 11/2007

OTHER PUBLICATIONS

Jul. 20, 2012 Search Report issued in International Patent Application No. PCT/US2012/033254.

(Continued)

*Primary Examiner* — Jonathan M Hurst
(74) *Attorney, Agent, or Firm* — Oliff PLC

(57) ABSTRACT

Disclosed is portable organ transportation system including a mobile cart and an organ container. At least one of the mobile cart and the organ container include a latch for releasably attaching the organ container to the mobile cart. The organ container may be a portable organ preservation device or a portable organ perfusion apparatus.

7 Claims, 6 Drawing Sheets

(56) References Cited

U.S. PATENT DOCUMENTS

| | | | | |
|---|---|---|---|---|
| 2007/0184545 A1* | 8/2007 | Plaats | .................. | A01N 1/02 |
| | | | | 435/284.1 |
| 2007/0190636 A1* | 8/2007 | Hassanein et al. | ........ | 435/284.1 |
| 2008/0017194 A1 | 1/2008 | Hassanein et al. | | |
| 2010/0290877 A1* | 11/2010 | Landau | .................. | B25H 3/028 |
| | | | | 414/490 |
| 2011/0049824 A1* | 3/2011 | Bar-Erez | ................ | B25H 3/023 |
| | | | | 280/47.18 |
| 2011/0073609 A1* | 3/2011 | Lesquir | ............. | B65D 25/2867 |
| | | | | 220/763 |

OTHER PUBLICATIONS

Jul. 20, 2012 Written Opinion issued in International Patent Application No. PCT/US2012/033254.

"LifePortation." Organ Recovery Systems. http://www.organ-recovery.com/products.php?id=2. Jun. 27, 2011.

May 13, 2013 International Preliminary Report on Patentability issued in International application No. PCT/US2012/033254.

Sep. 24, 2014 Office Action issued in Chinese Application No. 201280029336.X.

May 28, 2015 Office Action issued in Chinese Application No. 201280029336.X.

* cited by examiner

PORTABLE ORGAN TRANSPORTATION SYSTEM

BACKGROUND

I. Related Technical Fields

Related technical fields include organ transportation systems and methods, and more specifically, a mobile cart and/or organ container and associated methods for attaching and detaching the organ container from the mobile cart.

II. Related Art

Recent advances in organ transplantation and preservation allow for organs to be donated at a location that is far from the recipient of the organ. As such, donated organs must be preserved over an extended time or distance. Portable organ transportation and/or preservation devices such as disclosed in U.S. Pat. No. 6,673,594 to Owen et al., which is hereby incorporated by reference, are known. With such devices, the viability, and thus distance the organ can be transported, can be greatly extended. Such organ transportation devices are used in the surgical suite where the organ is donated, in transport, and in the surgical suite where the organ is transplanted.

SUMMARY

In the surgical suites, space is at a premium. Space for every medical device, the surgical team, and the patient must be provided. When transporting an organ in an organ transporter, space must be available in the transporting vehicle, be it an automobile, aircraft, or the like. The organ transporter must also be readily and securely conveyed between the surgical suite and the transporting vehicle. Each of the locations where the organ transporter is used has specific needs. For example, it is undesirable for a table or bench to be required specifically for the organ transporter in the surgical suite because it uses valuable space and the transporter can be knocked off of the table or bench. Similarly, it is preferred for the organ transporter to be conveniently located by the donor or recipient of the organ. Space in the transporting vehicle can be even more precious because the vehicles can be relatively small, especially if the vehicle is an aircraft. Therefore, it is undesirable for an organ transportation device to take up too much precious space in these situations.

Further, although there is a general trend toward smaller organ transport devices, certain organs, such as livers, are relatively large and may require a larger organ transport device than smaller organs, such as kidneys. Such relatively larger organ transport devices may require a two person lift due to weight or size.

Exemplary implementations of the broad inventive principles described herein provide a portable organ transportation system including a mobile cart and an organ container. At least one of the mobile cart and the organ container include a latch for releasably attaching the organ container to the mobile cart. These broad inventive principles provide a solution to the problems described above because the combination of a mobile cart and portable organ transportation system provides the flexibility to address the space constraints discussed above while maintaining mobility, convenience, and secure transport.

Exemplary implementations of the broad inventive principles described herein provide the organ container with a first handle and a second handle. The first handle is configured to facilitate pushing the mobile cart while the organ container is attached to the mobile cart. The second handle is configured to allow at least two people to lift and carry the organ container and attaching the organ container to, or detaching the organ container from, the mobile cart without having to let go of the container. These broad inventive principles facilitate the secure movement of the portable organ transportation system within the surgical suite, movement to or from the transportation vehicle, as well as loading or unloading the vehicle.

Exemplary implementations of the broad inventive principles described herein provide an organ container with a handle and at least two attachment units that are configured so that a user can separately actuate at least two of the attachment units while continuing to grip the handle with two hands. This is advantageous in that it allows a user to detach the organ container from the cart while safely and securely holding the organ container.

BRIEF DESCRIPTION OF THE DRAWINGS

Exemplary implementations can be described with reference to the following figures wherein.

DETAILED DESCRIPTION

Figure 1:
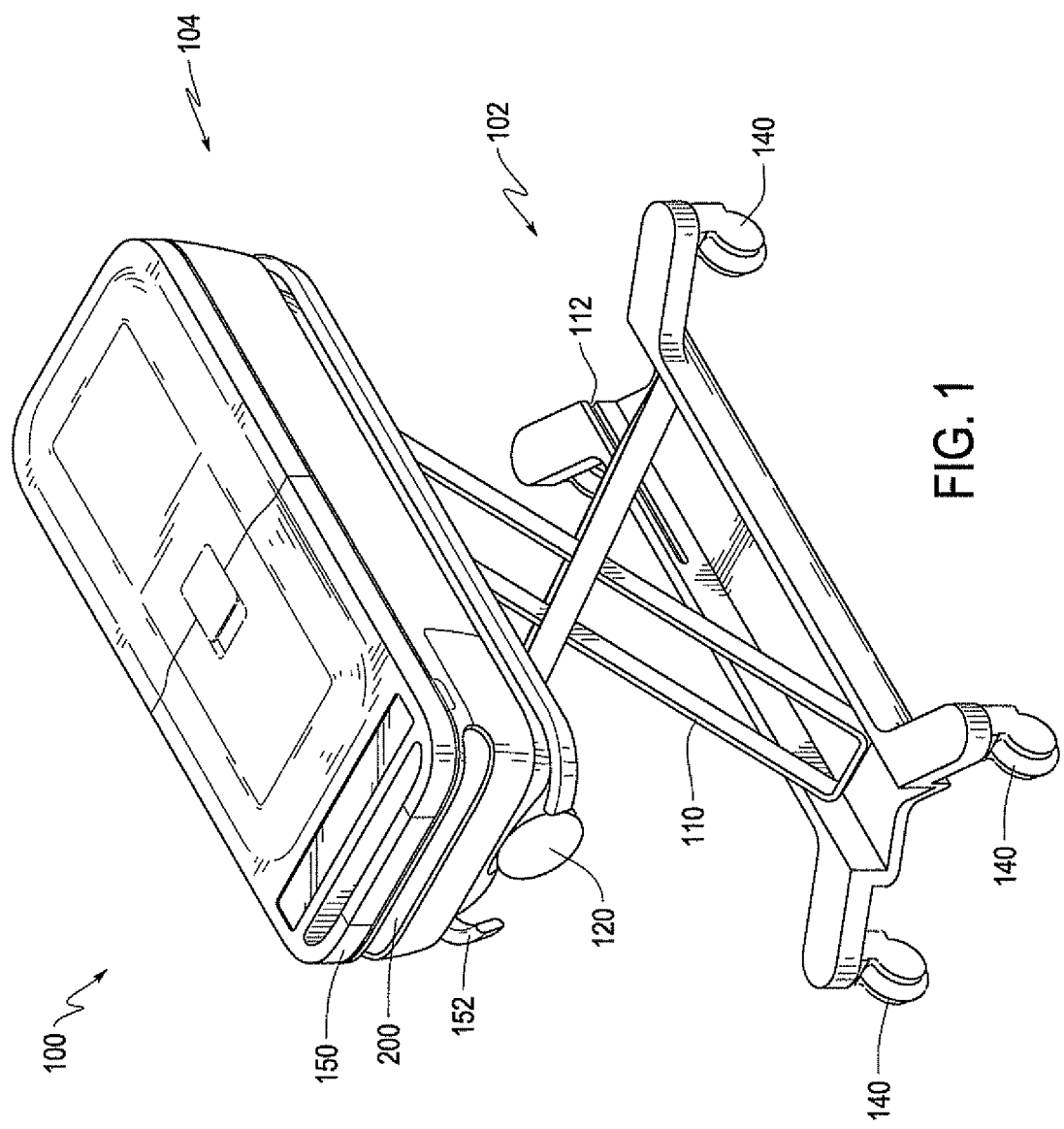
FIG. 1 illustrates a perspective view of a portable organ transportation system.

FIG. 1 shows a top perspective view of a portable organ transportation system 100. The organ transportation system 100 preferably includes a mobile cart 102 and an organ container 104. The organ container may be a portable preservation device or a portable organ perfusion apparatus as disclosed in U.S. Pat. No. 6,673,594.

Figure 2:
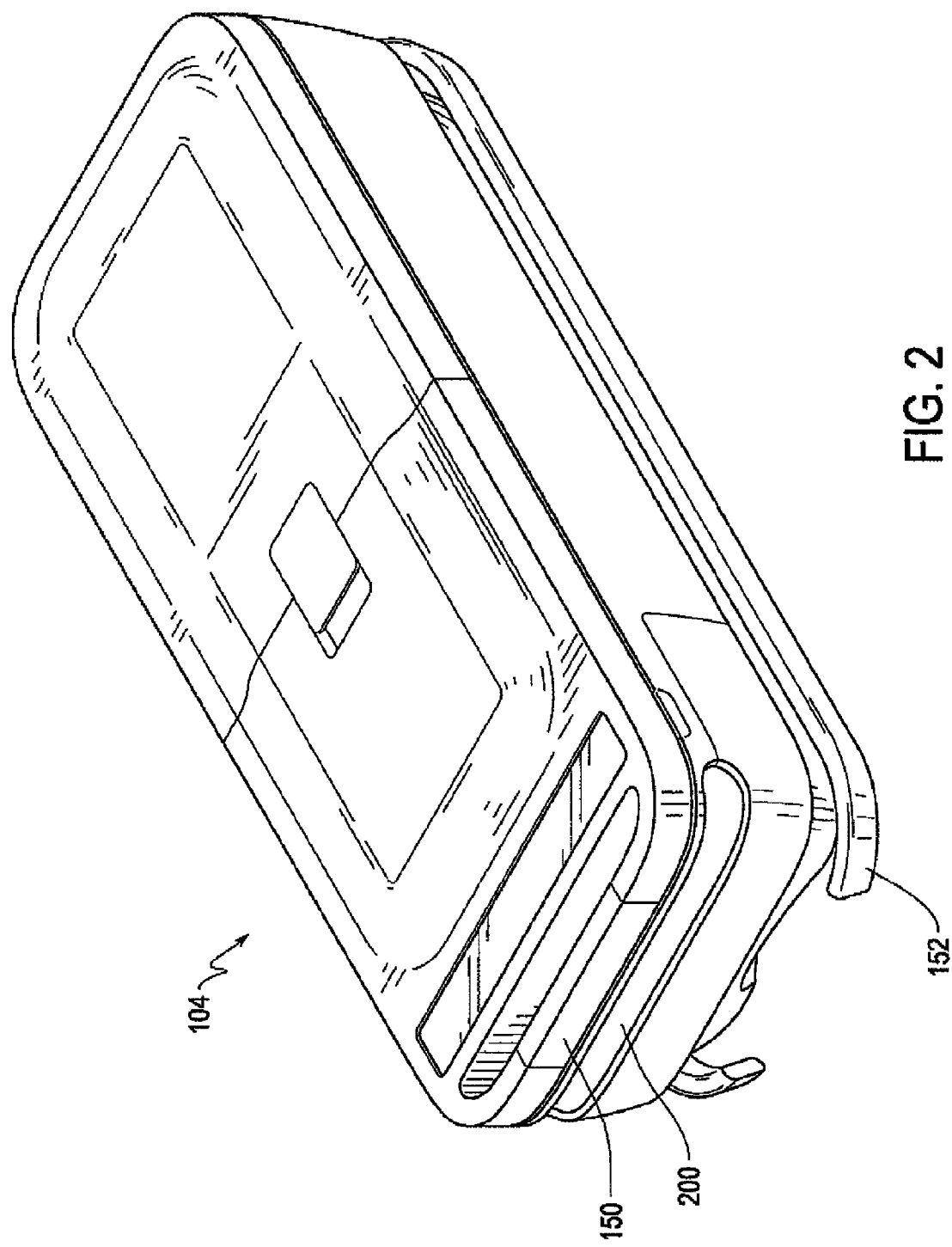
FIG. 2 illustrates a top perspective view of an organ container.

The organ container 104 is shown in a perspective view in FIG. 2. The organ container may include a first handle 150 and a second handle 152. These two handles each provide different advantages.

The first handle 150 is shown near a top portion of the organ container 104 and disposed on an end. One advantage of locating the first handle 150 in this manner is to facilitate pushing the organ transportation system 100 when the organ container 104 is on the mobile cart 102. A user readily grasps this location while pushing the organ transportation system 100. Other locations of the first handle may be chosen by one of ordinary skill and still be within the broad inventive principles described herein.

The second handle 152 is shown near the bottom of the organ container 104. The second handle is shown to wrap substantially continuously around most of the periphery the organ container 104, with a small section broken out to facilitate actuation of the hand crank 120 on the mobile cart (shown in FIG. 1). If the hand crank 120 is omitted, the second handle may wrap around the entire periphery of the organ container 104. Alternatively, the second handle can be any number of handles to facilitate the needs of a user. With a location as illustrated, the second handle 152 may be particularly suited for lifting the organ container 104 by two people. The second handle 152 as illustrated provides ample room for more than one person to grasp the handle with at least one hand per person, preferably two hands per person.

Figure 3:
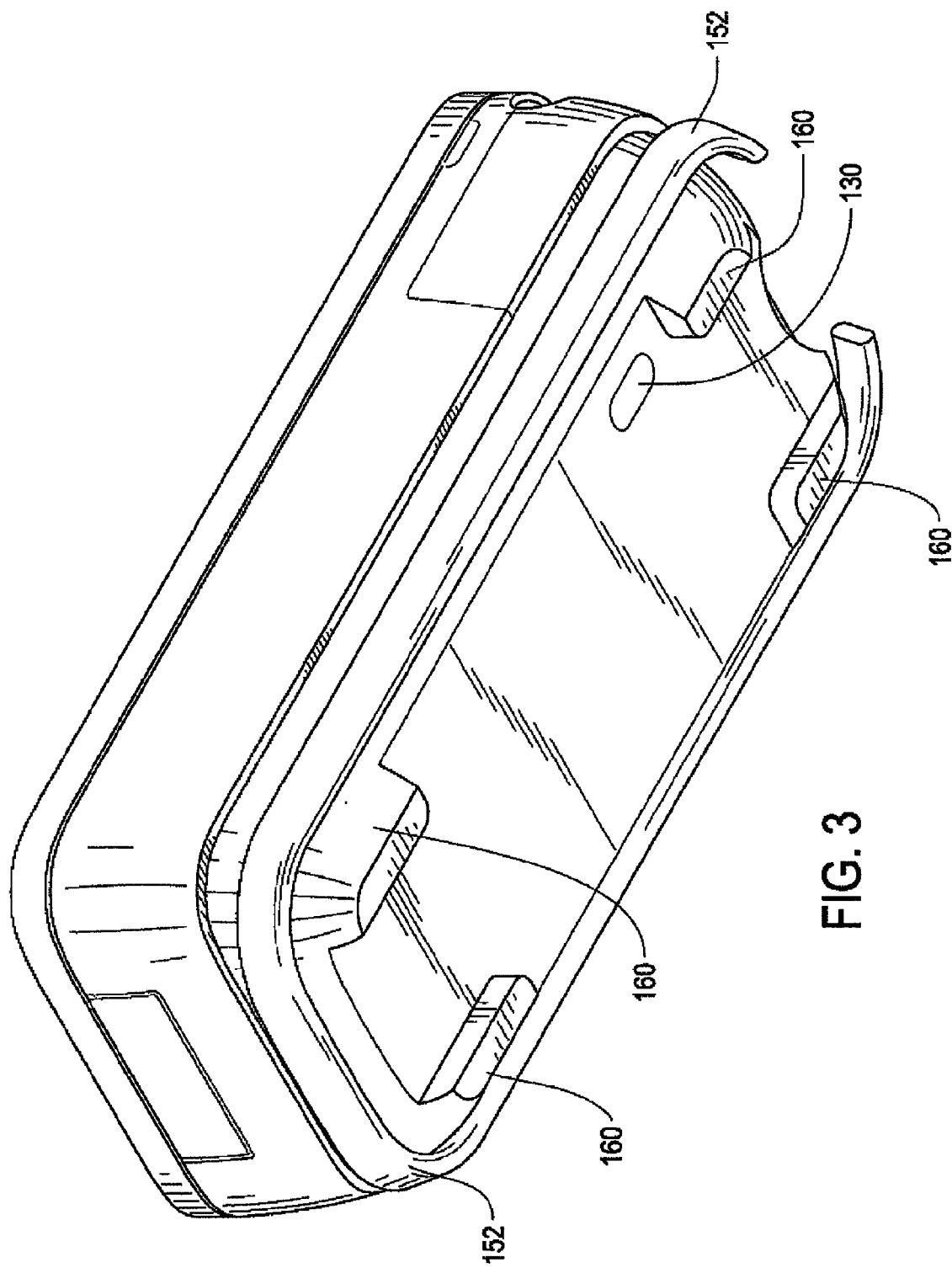
FIG. 3 illustrates a bottom perspective view of an organ container.

FIG. 3 illustrates the organ container in a bottom perspective view. Four of the protrusions 160 are visible, with one being located generally at each corner of the organ container 104. As shown, the protrusions 160 serve to locate and/or align the organ container 104 with the mobile cart 102 when the organ container 104 is on the mobile cart 102. Also, the protrusions 160 may serve to keep the organ container 104 raised off of a surface when the organ container is placed on such a surface. The protrusions 160 and the second handle 152 are preferably disposed relative to one another such that a user's hand can fit under and grasp the second handle 152 when the organ container is removed from the mobile cart 102 and placed on a surface.

The mobile cart 102 includes structure that is complementary to and accepts the protrusions 160 to locate the organ container 104 on the mobile cart 102. The complementary structure is illustrated as cut outs 166. Four of the cut outs 166 are illustrated, but any number can be chosen so long the out outs 166 are chosen to cooperate with the protrusions 160 to locate the organ container 104.

Figure 4:
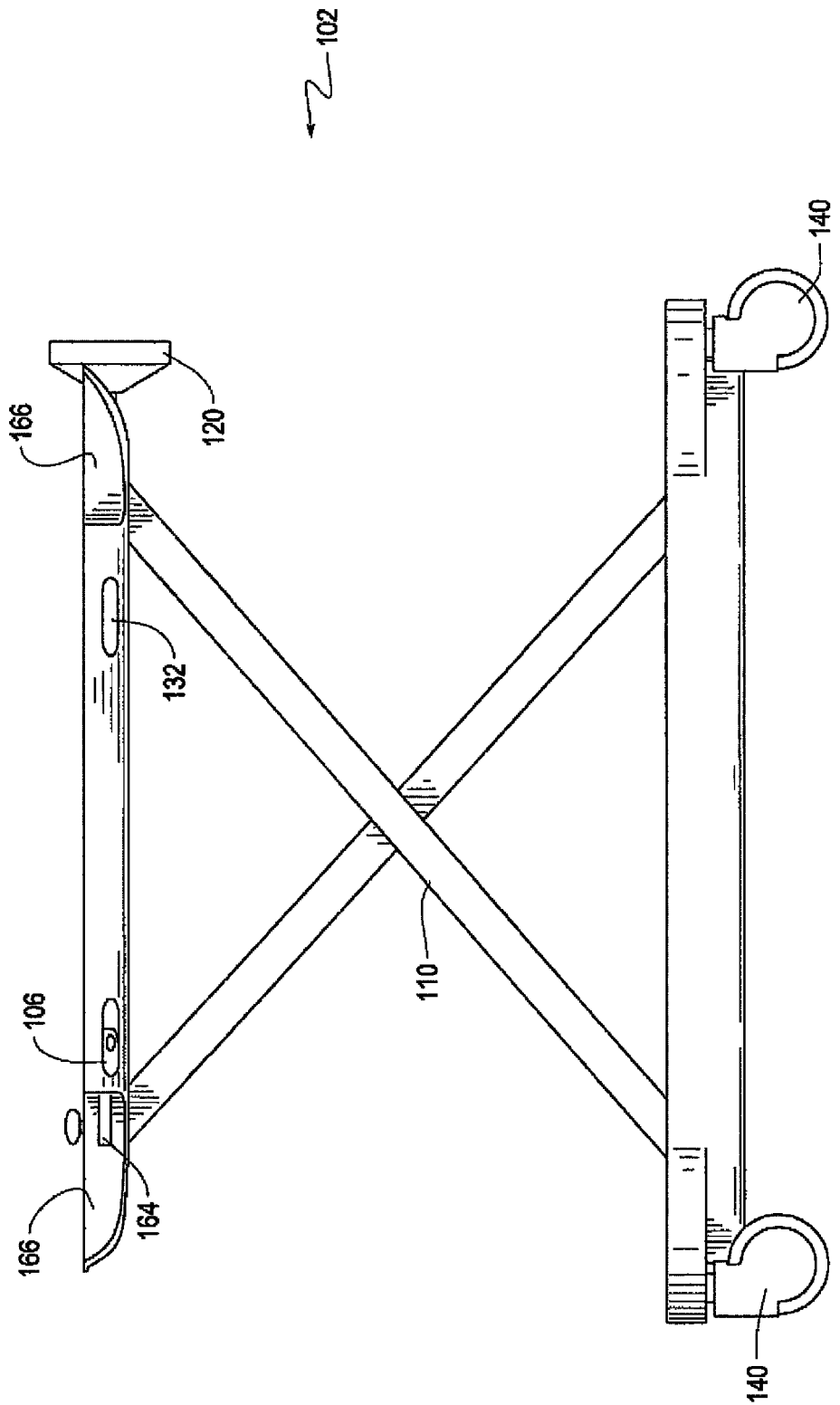
FIG. 4 illustrates a side view of a mobile cart.

A side view of the mobile cart 102 is illustrated in FIG. 4. The mobile cart 102 includes a height adjusting structure 110. The height adjusting structure 110 is shown in a partially expanded state, and is capable of being raised to a higher position, as well as being lowered into a collapsed position. The height is adjustable based upon the needs of a user. For example, in an operating suite, the mobile cart 102 may be raised to near its maximum height. In a transportation vehicle, the mobile cart 102 may be fully collapsed to reduce an overall size of the organ transportation system 100 and to lower the center of gravity to reduce the likelihood of tipping.

The height adjusting structure 110 may include four bars in an X-shaped linkage similar to a scissor lift. In order to facilitate an X-shaped linkage raising or lowering the height of the mobile cart 102, a sliding channel 112 may be included in a bottom portion of the mobile cart. A similar structure may be provided in a top portion of the car. The broad inventive principles described herein contemplate other structures for adjusting a height of the mobile cart 102. For example, the height adjusting structure could some sort of hydraulic lifting mechanism or other mechanism expandable by pressurized fluid. Alternatively, the height adjusting structure 110 may include screws that expand a height of the mobile cart 102.

A hand crank 120 may be included to manually drive a lead screw and adjust a height of the height adjusting structure 110. Alternatively, an electric motor (not shown) may be included to adjust the height. In either scenario, the linkage may include a slider that disengages from the lead screw when a latch is released, which allows the height adjusting structure to be reduced to a minimum height or to collapse. The latch catches automatically when the cart is raised from a collapsed state and automatically rethreads the lead screw when the hand crank 120 or electric motor is rotated.

Figure 5:
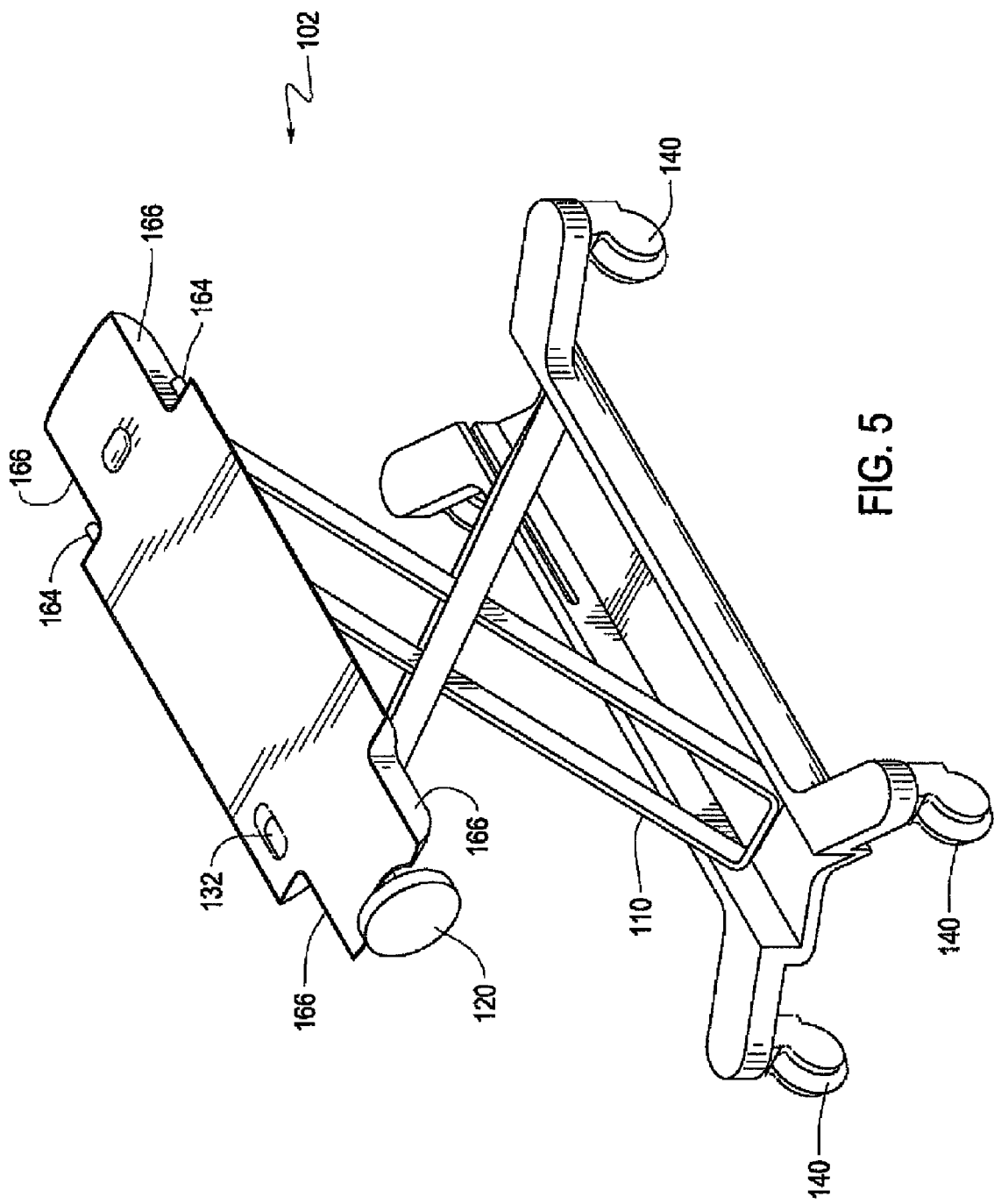
FIG. 5 illustrates a top perspective view of a mobile cart.

FIG. 3 illustrates a location for a power connector 130 used to provide power to the electric motor. FIG. 5 illustrates a corresponding location when a pass through hole may be located for connecting an electrical cable to the power connector 130 or where a mating power connector may be located on the mobile cart.

The mobile cart 102 may also include wheels 140. The wheels 140 may be removable or otherwise displaceable so that the wheels 140 can be placed in a location that requires less space. This is beneficial in applications where there is limited space for the organ transportation system 100. Preferably, the wheels 140 are lockable to prevent the mobile cart from moving.

Figure 6:
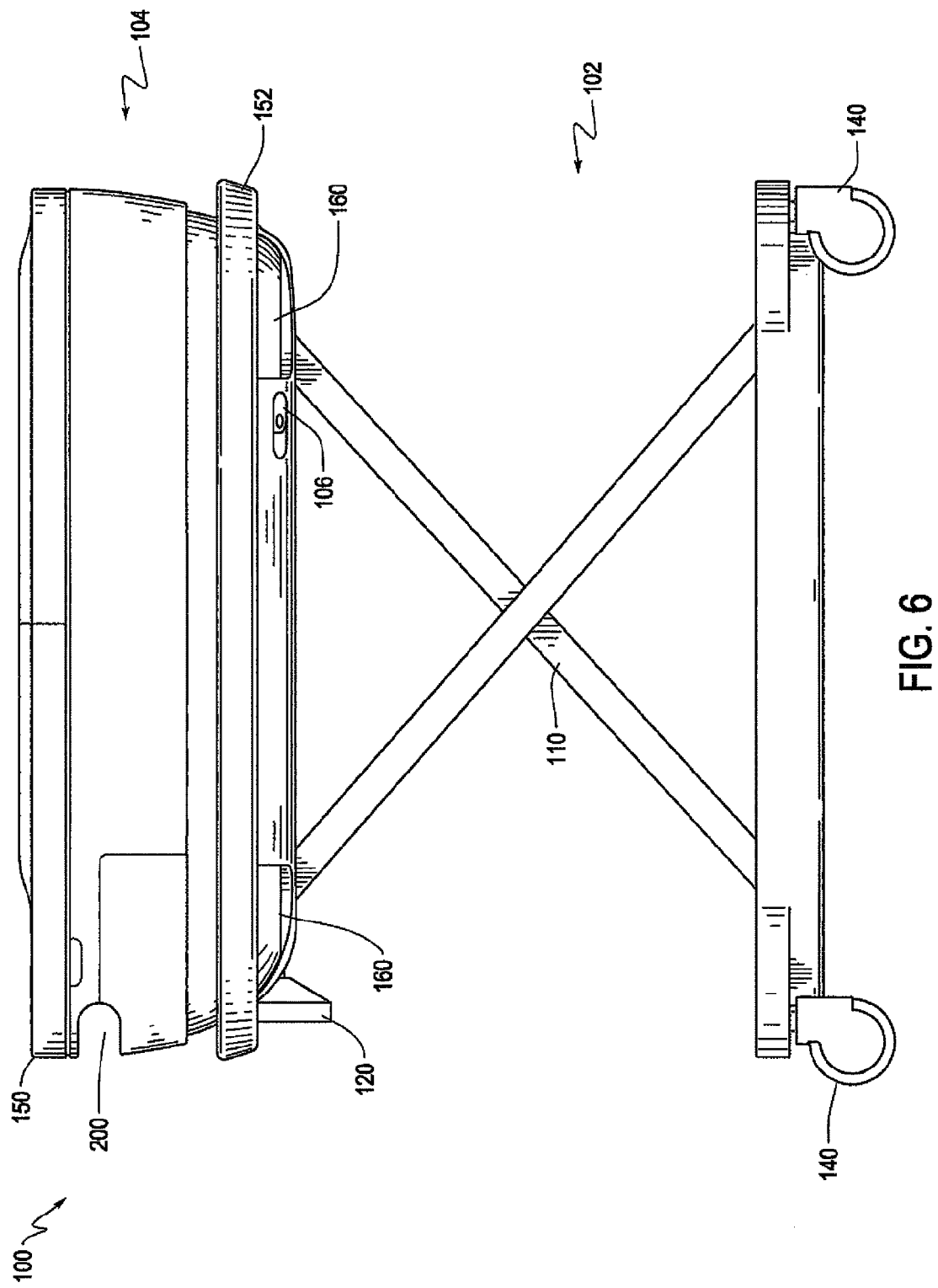
FIG. 6 illustrates a side view of a portable organ transportation system.

FIGS. 5 and 6 illustrate additional features related to mounting the organ container 104 to the mobile cart 102. Preferably a latch 106 is located on either the mobile cart 102 or the organ container 104. Each latch 106 that is included may be configured to releasably attach the organ container to the mobile cart. FIG. 6 illustrates a latch 106 including a pin 164 as illustrated in FIG. 4, both of which are illustrated as being located on the mobile cart 102. The broad inventive principles described herein contemplate various other locations for the latch on the organ container 104 as well.

The latch 106 may include a hole shaped to allow a user to insert a finger into that hole to actuate the latch 106 and release the pin 164, preferably by sliding, from a mating hole in the organ container (not shown). The hole in the organ container may be located in one or more of the protrusions 160. Preferably, the latch is located so the latch can be actuated by a user's hand while that hand is grasping the second handle 152. The figures illustrate one latch 106 on each side of the mobile cart 102 for a total of two latches 106, but any alternative number of latches 106, including one, three, or four, may be included based upon the needs of a user. Preferably, for each latch 106, the second handle 152 includes a corresponding portion to allow a user to grasp the second handle 152 near each latch 106 and actuate that latch. As such, multiple users may simultaneously grip the second handle 152 and actuate at least one latch 106. After the latches 106 are actuated, the organ container 104 may be readily lifted and removed from the mobile cart 102. This way, the organ container 104 can be securely handled at all times, including during latching and unlatching from the mobile cart 102.

The latch 106 as illustrated and described above is mechanically actuated. Alternatively, the latches may be electronically actuated. This may be advantageous in that it increases ease of use or the electronic actuation can provide lock out or tamper proof features so that only an authorized user may release the latch 106.

The organ container may also include a pocket 200. The pocket 200 may be configured to contain documents related to the organ transporter. Such a pocket 200 is advantageous because important documentation may frequently be included with a donated organ. The pocket 200 allows for a secure location to keep the documentation with the organ at all times. The pocket 200 may also include a lid or cover (not shown) to prevent unwanted foreign objects, such as liquid or debris, from entering the pocket as well as retaining any document placed in the pocket.

While various features have been described in conjunction with the examples outlined above, various alternatives, modifications, variations, and/or improvements of those features and/or examples may be possible. Accordingly, the examples, as set forth above, are intended to be illustrative. Various changes may be made without departing from the broad spirit and scope of the underlying inventive principles.

What is claimed is:
1. A portable organ transportation system, comprising:
an organ container comprising a handle and inner and outer surfaces, the handle being fixed in position relative to the organ container and located adjacent to opposed ones of the outer surfaces, and the inner surfaces defining a space configured to hold a donor organ;

a mobile cart; and at least two attachment units that attach the organ container to the mobile cart, wherein:

each of the at least two attachment units is disposed at least partially on at least one said outer surface of the organ container, the at least two attachment units are configured so that one or more users can separately actuate the at least two attachment units while gripping the handle with two hands to attach or detach the organ container from the mobile cart, and the organ container includes a portable organ perfusion apparatus configured to perfuse, even when the organ container is not attached to the mobile cart, the donor organ holdable within the space of the organ container.

2. The portable organ transportation system according to claim 1, wherein:

the at least two attachment units are configured so that a single user can separately actuate the at least two attachment units while gripping the handle with two hands to attach or detach the organ container from the mobile cart.

3. The portable organ transportation system according to claim 1, wherein:

the at least two attachment units are configured so that:
a first one of the at least two attachment units can be actuated by a hand of a first user while that first user hand is gripping the handle; and
a second one of the at least two attachment units can be actuated by a hand of a second user while that second user hand is gripping the handle.

4. The portable organ transportation system according to claim 1, wherein the handle is separate from an actuation portion of the attachment unit that can be manipulated by the user to attach or detach the organ container from the mobile cart.

5. A method of separating an organ container from a mobile cart, comprising:

grasping a handle of the organ container with a first hand, the handle being fixed in position relative to the organ container and located adjacent to opposed ones of outer surfaces of the organ container;

grasping the handle with a second hand;

actuating a first mechanism with the first hand to release a latch attaching the organ container to the mobile cart while continuing to grasp the handle with the first hand;

actuating a second mechanism with the second hand to release a latch attaching the organ container to the mobile cart while continuing to grasp the handle with the second hand; and removing the organ container from the mobile cart, wherein:

the organ container includes inner surfaces and the outer surfaces, the inner surfaces defining a space configured to hold a donor organ, the first mechanism is disposed at least partially on at least one said outer surface of the organ container, and the organ container includes a portable organ perfusion apparatus configured to perfuse, even when the organ container is not attached to the mobile cart, the donor organ holdable within the space of the organ container.

6. The method according to claim 5, wherein the first hand and the second hand are hands of different users.

7. The method according to claim 5, wherein the first hand and the second hand are hands of a single user.

* * * * *